United States Patent
Munnelly et al.

(10) Patent No.: US 9,615,922 B2
(45) Date of Patent: Apr. 11, 2017

(54) METHOD AND APPARATUS FOR PREPARING A CONTOURED BIOLOGICAL TISSUE

(71) Applicant: Edwards Lifesciences Corporation, Irvine, CA (US)

(72) Inventors: Amy E. Munnelly, Irvine, CA (US); Jeffrey S. Dove, Santa Ana, CA (US); Minsey Lee, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 115 days.

(21) Appl. No.: 14/485,576

(22) Filed: Sep. 12, 2014

(65) Prior Publication Data
US 2015/0091219 A1   Apr. 2, 2015

Related U.S. Application Data

(60) Provisional application No. 61/884,775, filed on Sep. 30, 2013.

(51) Int. Cl.
*A61F 2/24*   (2006.01)
(52) U.S. Cl.
CPC ...... *A61F 2/2415* (2013.01); *A61F 2240/004* (2013.01)
(58) Field of Classification Search
CPC . A61F 2/2412; A61F 2/2415; A61F 2240/004
See application file for complete search history.

(56) References Cited

U.S. PATENT DOCUMENTS 2,393,580 A   1/1946   Weiskopf
4,120,649 A   10/1978  Schechter
(Continued)

FOREIGN PATENT DOCUMENTS

EP   0169259 A1   1/1986
EP   2394673 A1   12/2011
(Continued)

OTHER PUBLICATIONS

International Search Report from corresponding PCT case No. PCT/US2014/055647 dated Dec. 29, 2014.
(Continued)

*Primary Examiner* — Charles A Marmor, II
*Assistant Examiner* — Carrie R Dorna
(74) *Attorney, Agent, or Firm* — Guy Cumberbatch; Pui Tong Ho

(57) ABSTRACT

An assembly and methods for providing a contoured biological tissue are described. The assembly comprises a first plate and a second plate. The first plate is configured to receive a biological tissue. The second plate is configured to apply a compressive force on the biological tissue that is disposed on the first plate. One or both of the first and second plates comprise a defined shape and a contoured area within the defined shape. The contoured area comprises at least first and second elevations and a continuous transition between the first and second transitions. One or more energy sources is associated with one or both of the first and second plates. The one or more energy sources delivers energy while the second plate applies the compressive force on the biological tissue disposed on the first plate.

25 Claims, 13 Drawing Sheets

(56) References Cited

U.S. PATENT DOCUMENTS

| | | |
|---|---|---|
| 4,323,358 A | 4/1982 | Lentz et al. |
| 4,350,492 A | 9/1982 | Wright et al. |
| 4,372,743 A | 2/1983 | Lane |
| 4,378,224 A | 3/1983 | Nimni et al. |
| 4,402,697 A | 9/1983 | Pollock et al. |
| 4,405,327 A | 9/1983 | Pollock |
| 4,481,009 A | 11/1984 | Nashef |
| 4,553,974 A | 11/1985 | Dewanjee |
| 4,624,822 A | 11/1986 | Arru et al. |
| 4,647,283 A | 3/1987 | Carpentier et al. |
| 4,648,881 A | 3/1987 | Carpentier et al. |
| 4,758,151 A | 7/1988 | Arru et al. |
| 4,770,665 A | 9/1988 | Nashef |
| 4,776,853 A | 10/1988 | Klement et al. |
| 4,786,287 A | 11/1988 | Nashef et al. |
| 4,838,888 A | 6/1989 | Nashef |
| 4,865,871 A | 9/1989 | Livesey et al. |
| 4,885,005 A | 12/1989 | Nashef et al. |
| 4,958,008 A | 9/1990 | Petite et al. |
| 4,976,733 A | 12/1990 | Girardot |
| 5,002,566 A | 3/1991 | Carpentier et al. |
| 5,051,401 A | 9/1991 | Sikes |
| 5,080,670 A | 1/1992 | Imamura et al. |
| 5,094,661 A | 3/1992 | Levy et al. |
| 5,104,405 A | 4/1992 | Nimni |
| 5,116,564 A | 5/1992 | Jansen et al. |
| 5,147,514 A | 9/1992 | Mechanic |
| 5,154,007 A | 10/1992 | Piunno et al. |
| 5,200,399 A | 4/1993 | Wettlaufer et al. |
| 5,215,541 A | 6/1993 | Nashef et al. |
| 5,279,612 A | 1/1994 | Eberhardt |
| 5,329,846 A | 7/1994 | Bonutti |
| 5,376,110 A * | 12/1994 | Tu .................. A61F 2/062 128/DIG. 8 |
| 5,397,353 A | 3/1995 | Oliver et al. |
| 5,437,287 A | 8/1995 | Phillips et al. |
| 5,447,536 A | 9/1995 | Girardot et al. |
| 5,460,962 A | 10/1995 | Kemp |
| 5,476,516 A | 12/1995 | Seifter et al. |
| 5,509,932 A | 4/1996 | Keogh et al. |
| 5,558,875 A | 9/1996 | Wang |
| 5,595,571 A | 1/1997 | Jaffe et al. |
| 5,613,982 A | 3/1997 | Goldstein |
| 5,645,587 A | 7/1997 | Chanda et al. |
| 5,674,298 A | 10/1997 | Levy et al. |
| 5,697,972 A | 12/1997 | Kim et al. |
| 5,713,953 A | 2/1998 | Vallana et al. |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,766,520 A | 6/1998 | Bronshtein |
| 5,769,780 A | 6/1998 | Hata et al. |
| 5,782,914 A | 7/1998 | Schankereli |
| 5,782,931 A | 7/1998 | Yang et al. |
| 5,843,180 A | 12/1998 | Jaffe et al. |
| 5,843,181 A | 12/1998 | Jaffe et al. |
| 5,855,620 A | 1/1999 | Bishopric et al. |
| 5,862,806 A | 1/1999 | Cheung |
| 5,873,812 A | 2/1999 | Ciana et al. |
| 5,899,936 A | 5/1999 | Goldstein |
| 5,911,951 A | 6/1999 | Girardot et al. |
| 5,919,472 A | 7/1999 | Trescony et al. |
| 5,921,980 A | 7/1999 | Kirn |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,993,844 A | 11/1999 | Abraham et al. |
| 6,008,292 A | 12/1999 | Lee et al. |
| 6,017,741 A | 1/2000 | Keogh |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |
| 6,166,184 A | 12/2000 | Hendriks et al. |
| 6,174,331 B1 | 1/2001 | Moe et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,293,970 B1 | 9/2001 | Wolfinbarger, Jr. et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,328,762 B1 | 12/2001 | Anderson et al. |
| 6,334,873 B1 | 1/2002 | Lane et al. |
| 6,352,708 B1 | 3/2002 | Duran et al. |
| 6,364,905 B1 | 4/2002 | Simpson et al. |
| 6,375,680 B1 | 4/2002 | Carlyle |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,475,239 B1 | 11/2002 | Campbell et al. |
| 6,479,079 B1 | 11/2002 | Pathak et al. |
| 6,482,199 B1 | 11/2002 | Neev |
| 6,491,511 B1 | 12/2002 | Duran et al. |
| 6,506,339 B1 | 1/2003 | Girardot et al. |
| 6,509,145 B1 | 1/2003 | Torrianni |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,589,591 B1 | 7/2003 | Mansouri et al. |
| 6,605,667 B1 | 8/2003 | Badejo et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,682,559 B2 | 1/2004 | Myers et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,872,226 B2 | 3/2005 | Cali et al. |
| 6,878,168 B2 | 4/2005 | Carpentier et al. |
| 6,908,591 B2 | 6/2005 | MacPhee et al. |
| 6,911,043 B2 | 6/2005 | Myers et al. |
| 6,919,172 B2 | 7/2005 | DePablo et al. |
| 7,008,763 B2 | 3/2006 | Cheung |
| 7,029,434 B2 | 4/2006 | Carpentier et al. |
| 7,037,333 B2 | 5/2006 | Myers et al. |
| 7,063,726 B2 | 6/2006 | Crouch et al. |
| 7,078,163 B2 | 7/2006 | Torrianni |
| 7,141,064 B2 | 11/2006 | Scott et al. |
| 7,143,769 B2 | 12/2006 | Stoltz et al. |
| 7,214,344 B2 | 5/2007 | Carpentier et al. |
| 7,238,200 B2 | 7/2007 | Lee et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,367,969 B2 | 5/2008 | Stoltz et al. |

(56) References Cited

U.S. PATENT DOCUMENTS

| | | | |
|---|---|---|---|
| RE40,570 E | 11/2008 | Carpentier et al. |
| 7,498,565 B2 | 3/2009 | Silberberg et al. |
| 7,579,381 B2 | 8/2009 | Dove |
| 7,594,974 B2 | 9/2009 | Cali et al. |
| 7,648,676 B2 | 1/2010 | Mills et al. |
| 7,682,304 B2 | 3/2010 | Heyninck-Jantz et al. |
| 7,914,569 B2 | 3/2011 | Nguyen et al. |
| 7,919,112 B2 | 4/2011 | Pathak et al. |
| 7,972,376 B1 | 7/2011 | Dove et al. |
| 8,007,992 B2 | 8/2011 | Tian et al. |
| 8,043,450 B2 | 10/2011 | Cali et al. |
| 8,075,615 B2 | 12/2011 | Eberhardt et al. |
| 8,105,375 B2 | 1/2012 | Navia et al. |
| 8,136,218 B2 | 3/2012 | Millwee et al. |
| 8,308,797 B2 | 11/2012 | Paniagua et al. |
| 8,361,144 B2 | 1/2013 | Fish et al. |
| 8,377,143 B2 | 2/2013 | Hamby et al. |
| 8,475,827 B2 | 7/2013 | Hamby et al. |
| 2001/0000804 A1 | 5/2001 | Goldstein et al. |
| 2001/0025196 A1 | 9/2001 | Chinn et al. |
| 2001/0027344 A1 | 10/2001 | Bonutti |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0091441 A1 | 7/2002 | Guzik |
| 2002/0111532 A1 | 8/2002 | Pathak et al. |
| 2003/0035843 A1 | 2/2003 | Livesey et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0212454 A1 | 11/2003 | Scott et al. |
| 2004/0030381 A1 | 2/2004 | Shu |
| 2004/0082991 A1 | 4/2004 | Nguyen et al. |
| 2004/0086543 A1 | 5/2004 | Keogh et al. |
| 2004/0158320 A1 | 8/2004 | Simionescu et al. |
| 2005/0010773 A1 | 1/2005 | Lapstun et al. |
| 2005/0119736 A1 | 6/2005 | Zilla et al. |
| 2005/0136510 A1 | 6/2005 | Hendriks et al. |
| 2005/0211680 A1 | 9/2005 | Li et al. |
| 2006/0084957 A1 | 4/2006 | Delfyett et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0193885 A1 | 8/2006 | Leonard Neethling et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2008/0302372 A1 | 12/2008 | Davidson et al. |
| 2008/0319166 A1 | 12/2008 | Shen |
| 2009/0041729 A1 | 2/2009 | Wolfinbarger, Jr. et al. |
| 2009/0130162 A2 | 5/2009 | Pathak et al. |
| 2009/0137999 A1 | 5/2009 | Silberberg et al. |
| 2009/0171424 A1 | 7/2009 | Britva et al. |
| 2009/0188900 A1 | 7/2009 | Cali et al. |
| 2009/0326524 A1 | 12/2009 | Cali et al. |
| 2010/0023119 A1* | 1/2010 | Yeo .................... A61F 2/2415 623/2.14 |
| 2010/0036484 A1 | 2/2010 | Hariton et al. |
| 2011/0092966 A1 | 4/2011 | Guo et al. |
| 2011/0177150 A1 | 7/2011 | Pathak et al. |
| 2011/0214398 A1 | 9/2011 | Liburd et al. |
| 2011/0238167 A1 | 9/2011 | Dove et al. |
| 2011/0251598 A1 | 10/2011 | Ozaki |
| 2011/0295363 A1 | 12/2011 | Girard et al. |
| 2011/0300625 A1 | 12/2011 | Paniagua et al. |
| 2011/0306124 A1 | 12/2011 | Strasly et al. |
| 2011/0311493 A1 | 12/2011 | Dove et al. |
| 2012/0035720 A1 | 2/2012 | Cali et al. |
| 2012/0059487 A1 | 3/2012 | Cunanan et al. |
| 2012/0067855 A1 | 3/2012 | Guo et al. |
| 2012/0078356 A1 | 3/2012 | Fish et al. |
| 2012/0095551 A1 | 4/2012 | Navia et al. |
| 2012/0123557 A1 | 5/2012 | Carpentier et al. |
| 2012/0185038 A1 | 7/2012 | Fish et al. |
| 2012/0328905 A1 | 12/2012 | Guo et al. |
| 2013/0012767 A1 | 1/2013 | Nguyen et al. |
| 2013/0122583 A1 | 5/2013 | Neethling |
| 2013/0134632 A1 | 5/2013 | Snedeker et al. |
| 2013/0238088 A1 | 9/2013 | Navia et al. |

FOREIGN PATENT DOCUMENTS

| | | |
|---|---|---|
| WO | 84/01894 A1 | 5/1984 |
| WO | 95/11047 A1 | 4/1995 |
| WO | 95/22361 A1 | 8/1995 |
| WO | 95/34332 A1 | 12/1995 |
| WO | 96/13227 A1 | 5/1996 |
| WO | 9807452 A1 | 2/1998 |
| WO | 9843556 A1 | 10/1998 |
| WO | 00/32252 A1 | 6/2000 |
| WO | 2004/082536 A1 | 9/2004 |
| WO | 2006026325 A2 | 3/2006 |
| WO | 2006099334 A2 | 9/2006 |
| WO | 2013009851 A2 | 1/2013 |

OTHER PUBLICATIONS

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as a Ligament Substitute," Journal of Biomedical Materials Research, vol. 21, No. 12, pp. 1383-1394, 1987, University of Arizona Health Science Center, Tucson, AZ.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./Feb. 2011.

Grabenwoger, M. et al. "Decreased Tissue Reaction to Bioprosthetic Heart Valve Material after L-glutamic acid Treatment. A Morphological Study." J. Biomed Mater. Res. Sep. 1992;26(9):1231-40.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Hauschka, P., et al., "Direct Identification of the Calcium- Binding Amino Acid, y-Carboxyglutamate, in Mineralized Tissue," Proc. Nat. Acad. Sci, vol. 72, No. 10, pp. 3925-3929, Oct. 1975.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

Liao, K., et al., "Mechanical Stress: An Independent Determinant of Early Bioprosthetic Calcification in Humans," Ann. Throac. Surg 2008;86:491-495.

Neethling, W, et al. Enhanced Biostability and Biocompatibility of Decellularized Bovine Pericardium, Crosslinked with an Ultra-Low Concentration Monomeric Aldehyde and Treated with ADAPT®, J. Heart Valve Dis. 2008; 17:456-464.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

(56) References Cited

OTHER PUBLICATIONS

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Trantina-Yates AE, et al. "Detoxification of Top Enhanced, Diamine-Extended Glutaraldehyde Fixation Significantly Reduces Bioprosthetic Root Calcification in the Sheep Model," J. Heart Valve Dis. Jan. 2003; 12(1):93-100.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

Al-Fagih, M.R., et al., "Aortic Valve Repair Using Bovine Pericardium for Cusp Extension," Journal of Thoracic and cardiovascular Surgery, vol. 9, No. 5, pp. 760-764, 1988.

Ohan, M., et al., "Glucose Stabilizes Collagen Sterilized with Gamma Irradiation," Wiley Periodicals, Inc., pp. 1188-1195, 2003.

\* cited by examiner

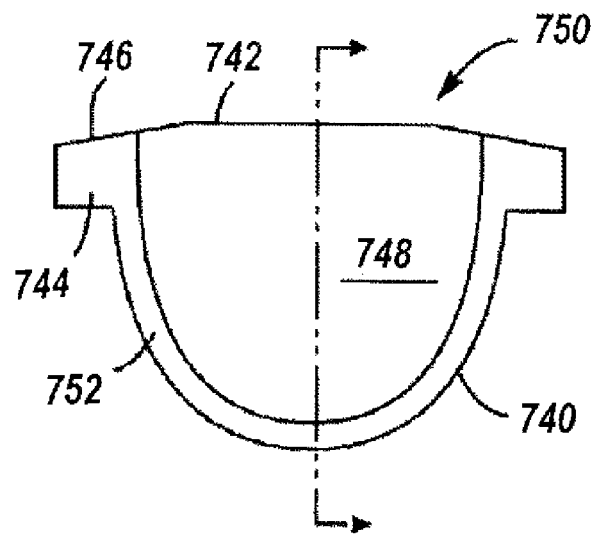
FIG. 7A
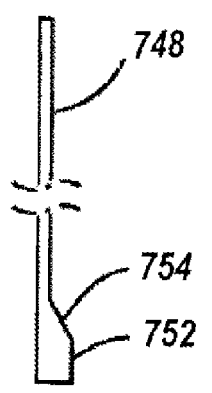 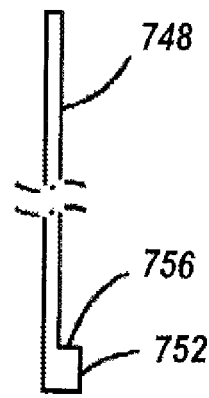
FIG. 7B    FIG. 7C

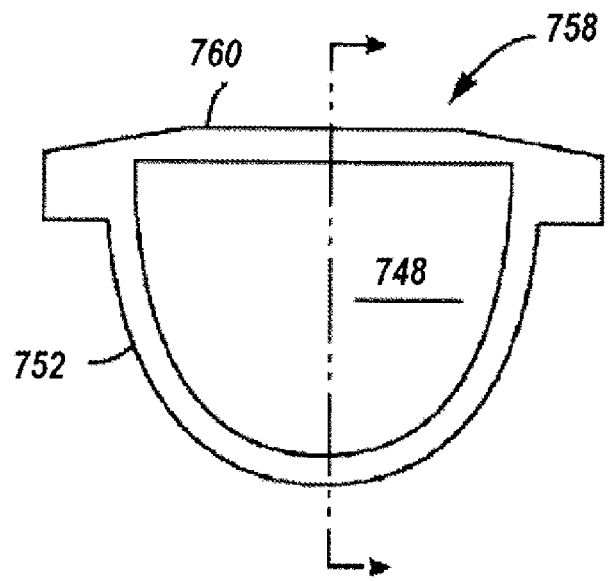
FIG. 8A
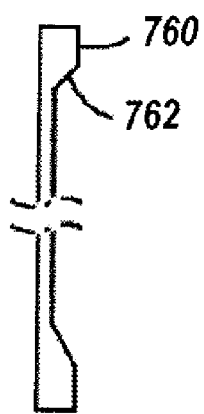 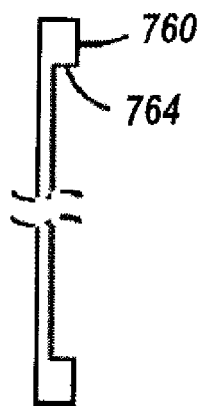
FIG. 8B     FIG. 8C

METHOD AND APPARATUS FOR PREPARING A CONTOURED BIOLOGICAL TISSUE

FIELD OF THE INVENTION

The present invention is directed to methods for treating bioprosthetic tissue for implantation in a patient and, more particularly, to methods for contouring and shaping biological tissue for use in connection with a bioprosthetic implant.

BACKGROUND

Minimally-invasive or percutaneous techniques for implanting bioprosthetic implants are commonly used in vascular and cardiovascular procedures. Such techniques involve the use of a delivery device, such as a catheter, to access a desired location via the patient's vasculature rather than using an open surgical approach where internal organs or tissue are exposed. The benefit of percutaneous procedures is in the ease of introducing devices into the patient without large cut downs, which can lead to long recovery times for patients.

One limitation of percutaneous procedures is the delivery profile of the bioprosthetic implant and delivery device. Because access to the desired implantation site is gained via the patient's vasculature, the delivery profile of the bioprosthetic implant and the delivery device, combined, must be sufficiently small so as to permit passage.

One method of reducing the delivery profile is to crimp the bioprosthetic implant about the delivery device. Crimping, however, may not reduce the delivery profile to a desired size due to the inherent bulk or configuration of the bioprosthetic implant. Therefore, changes are often required to the material and/or construction of the implantable bioprosthesis to permit crimping to yet smaller delivery profiles.

Replacement heart valves, for example, comprise a leaflet structure and a support structure. The leaflet structure is typically made from biological tissue, such as bovine pericardium, and the thickness of the tissue that makes up the leaflet structure limits the extent to which the heart valve can be crimped. Additionally, biological tissue will typically exhibit variations in thicknesses and these variations often produce unpredictable results with respect to the delivery profile of the crimped valves.

While the use of artificial or polymeric materials can offer a greater degree of control and flexibility to the resulting thickness of the material used for bioprosthetic implants, such materials may not always be desirable from at least a hemodynamic standpoint and may require the patient to take anticoagulants to prevent adverse effects from the interaction of the artificial material and the blood.

Another option is to remove excess portions of biological tissue so as to provide a thinner tissue having a consistent thickness throughout. The loss of tissue, however, can undesirably compromise the fiber structure and therefore the strength of the tissue. Compression of the tissue to produce a thinner tissue may be desirable. The compressed tissue, however, may spring back to its original and uneven thickness after compressive forces are released.

Therefore, what is needed are methods and devices for preparing a biological tissue adapted for a bioprosthetic implant and which reliably reduces the delivery profile for use in minimally-invasive and percutaneous procedures.

BRIEF SUMMARY

The preferred embodiments described herein are directed to methods for treating biological tissue for use in connection with an implantable bioprosthesis. The entire disclosure of U.S. Patent Pub. No. 2011/0238167, published Sep. 29, 2011, to Edwards Lifesciences, Inc. is incorporated herein by reference in its entirety.

In one embodiment, an assembly for providing a contoured biological tissue is provided. The assembly comprises a first plate and a second plate. The first plate is configured to receive a biological tissue. The second plate comprises a surface and is configured to apply a compressive force on the biological tissue that is disposed on the first plate. One or both of the first and second plates comprise a defined shape and a contoured area within the defined shape. The contoured area comprises at least first and second elevations and a continuous transition between the first and second transitions. One or more energy sources is associated with one or both of the first and second plates. The one or more energy sources delivers energy while the second plate applies the compressive force on the biological tissue. The second plate can contact the biological tissue directly or indirectly.

In accordance with a first aspect, one or both of the first and second plates are porous.

The defined shape can be one or a plurality of heart valve leaflets, having a substantially straight free edge and an arcuate cusp edge.

The first elevation can be defined along the arcuate cusp edge and the second elevation can be located between the arcuate cusp edge.

The first elevation can be higher relative to the second elevation, or the second elevation can be higher relative to the first elevation.

The assembly can further comprise a spacer disposed between the first and second plates, the spacer controlling a thickness of the compressed biological tissue. A blade corresponding substantially to the defined shape on the first plate can also be included. The energy delivered by the one or more energy sources is preferably one or a combination selected from the group consisting of: thermal, ultrasound, electromagnetic, vibrational, hydraulic, piezoelectric, pneumatic, and acoustic and sound energy. In one embodiment, the energy is thermal energy and the one or more energy sources is one or a combination selected from the group consisting of: thermal coils disposed within the first plate, thermal coils disposed within the second plate, and a liquid bath. In another embodiment, the energy is electromagnetic energy and the one or more energy sources is a RF or microwave antenna embedded in a non-conducting plate or a printed circuit antenna insulated from the tissue. In yet another embodiment, the energy is vibrational energy and the one or more energy sources is a clamp coupled to one or both of the first and second plates, a platform in contact with one or both of the first and second plates, or an actuator coupled to one or both of the first and second plates.

In some embodiments, the first plate comprises the defined shape and contoured area and the second plate comprises a substantially flat surface. Alternatively, the first and second plates can each comprise the defined shape and the contoured area within the defined shape.

In another embodiment, a method for preparing a contoured biological tissue is provided. The method comprises compressing a layer of biological tissue to reduce a thickness of at least a portion of the tissue and delivering energy from an energy source to one or both of the first and second plates during the compressing. The tissue following the compressing has at least two areas of different thicknesses and a continuous transition within the defined shape.

The method can further comprise treating the tissue with a first fixative to at least partially fix the tissue before, during and/or after the compressing. The first fixative can be glutaraldehyde.

The method can also include treating the tissue with a second fixative, the second fixative being one or a combination selected from the group consisting of: polyvinyl alcohols, polyetheramines, polyethyleneimine, di- or polyamines, polyurethanes, polyepoxies, polysiloxanes, polyacrylates, polyesters, poly block isobutylene-co-maleic acid, collagen, elastin, fibrin, hyaluronic acid, dextrin, genapin, di- or poly-alkynes, di- or poly-azides, and tannins. The fixative is a 0.1% polyetheramine solution having an average molecular weight of about 600 and a pH of about 6 to 9.

Other objects, features and advantages of the described preferred embodiments will become apparent to those skilled in the art from the following detailed description. It is to be understood, however, that the detailed description and specific examples, while indicating preferred embodiments of the present disclosure, are given by way of illustration and not limitation. Many changes and modifications within the scope of the present disclosure may be made without departing from the spirit thereof, and the disclosure includes all such modifications.

BRIEF DESCRIPTION OF THE DRAWINGS

Illustrative embodiments of the present disclosure are described herein with reference to the accompanying drawings, in which:

FIG. 7A is a plan view of a prosthetic heart valve leaflet having a thickened peripheral edge in areas where sutures penetrate for attachment to a structural stent;

FIGS. 7B and 7C are sectional views through a radial midline of the leaflet of FIG. 7A showing two different profiles;

FIG. 8A is a plan view of a prosthetic heart valve leaflet having a thickened peripheral edge in areas where sutures penetrate for attachment to a structural stent as well as a thickened free edge to reduce the risk of elongation at that location;

FIGS. 8B and 8C are sectional views through a radial midline of the leaflet of FIG. 8A showing two different thickness profiles;

Like numerals refer to like parts throughout the several views of the drawings.

DETAILED DESCRIPTION OF THE PREFERRED EMBODIMENTS

Specific, non-limiting embodiments of the apparatus and methods for contouring bioprosthetic tissue will now be described with reference to the drawings. It should be understood that such embodiments are by way of example only and merely illustrative of but a small number of embodiments within the scope of the present disclosure. Various changes and modifications obvious to one skilled in the art to which the present disclosure pertains are deemed to be within the spirit, scope and contemplation of the present disclosure as further defined in the appended claims.

Figure 1A:
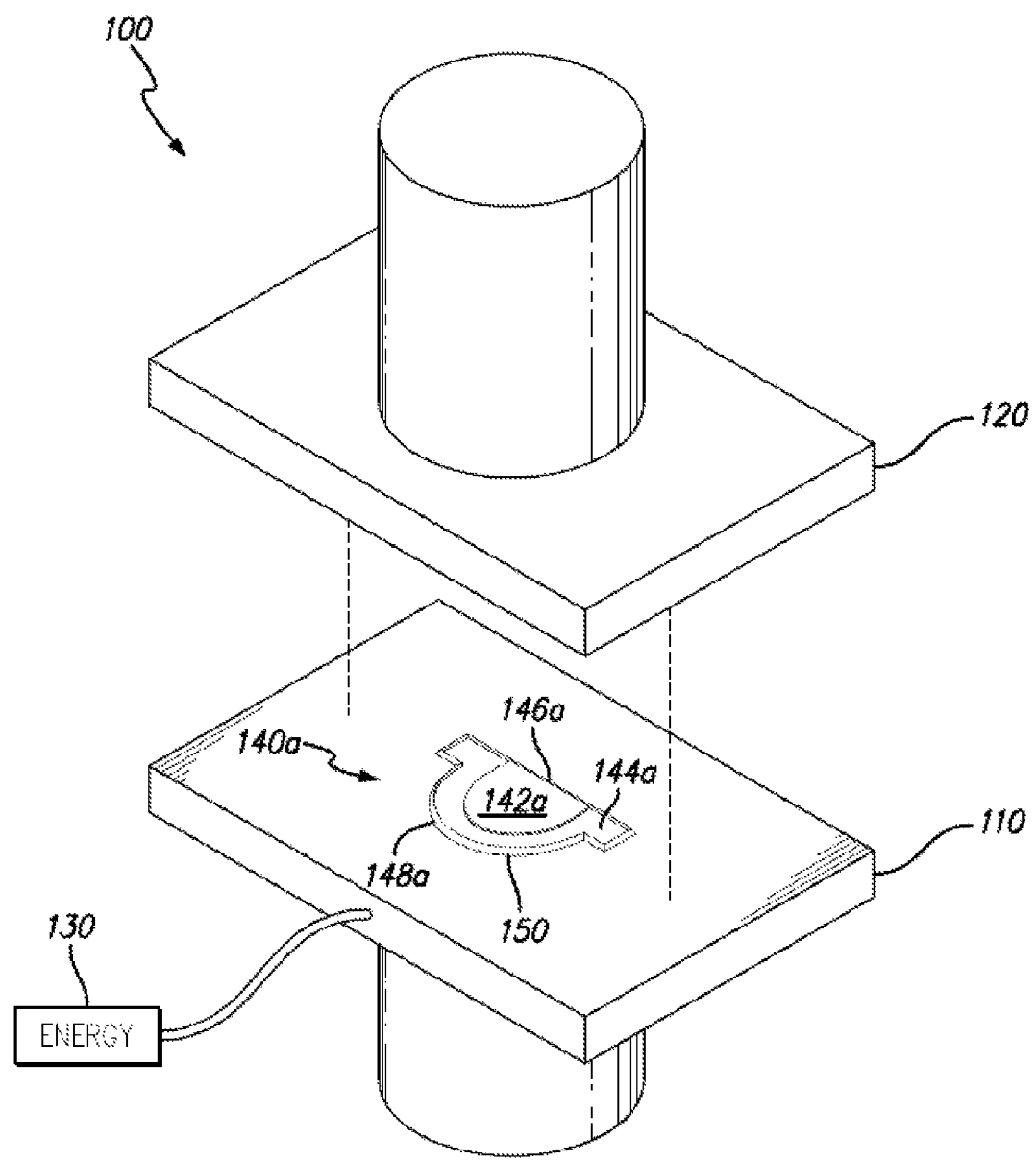
FIG. 1A is an exploded perspective view of an embodiment of an energized tissue compression assembly.

FIG. 1A depicts an energized tissue compression assembly 100 comprising a first bottom plate 110 and a second top plate 120. Each one of the first and second plates 110, 120 is coupled to an actuator (not depicted) which controllably displaces the first and second plates 110, 120 towards one another in direct physical contact and away from one another to release the compressed tissue (not shown).

Figure 1B:
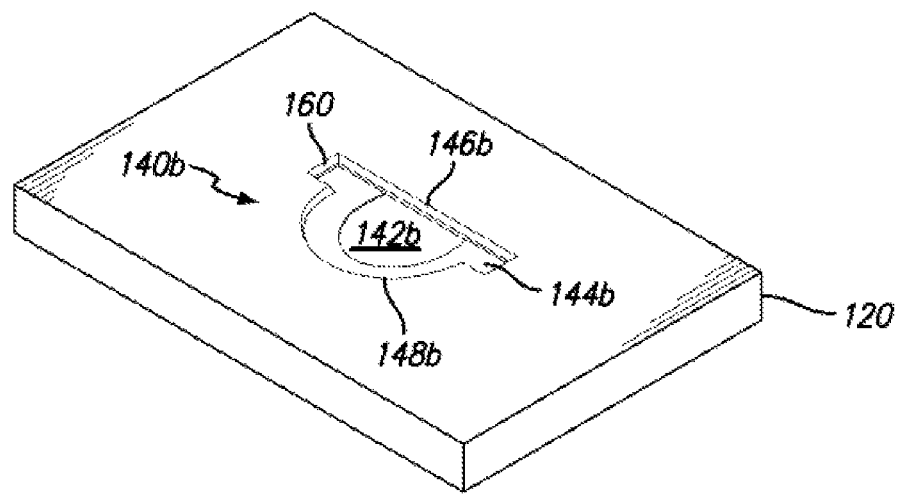
FIG. 1B is a perspective view of the bottom surface of the top compression plate of FIG. 1A.
Figure 1C:
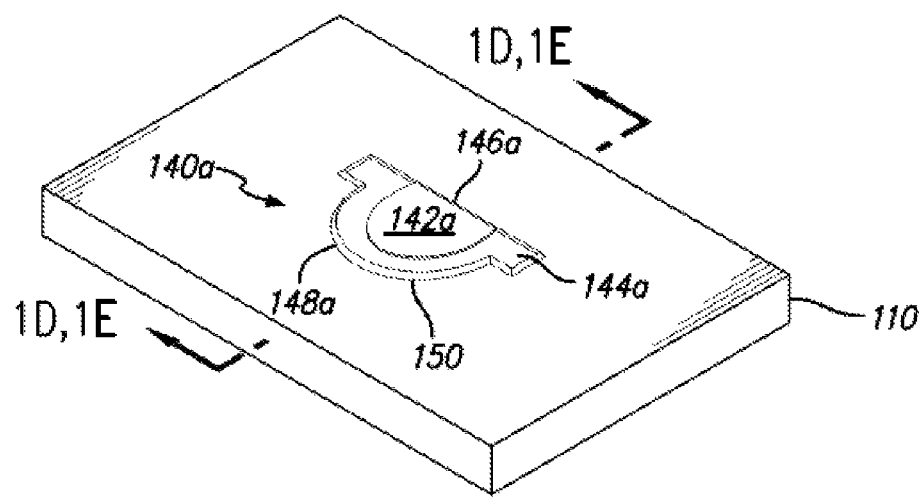
FIG. 1C is a perspective view of the top surface of the bottom compression plate of FIG. 1A.

Either one or both of the first and second plates 110, 120 can comprise a defined shape. In the embodiment depicted in FIGS. 1A-1C, both first and second plates 110, 120 comprise corresponding defined shapes in the form of a single heart valve leaflet 140a,b. The shape of the heart valve leaflet 140a,b depicted in FIGS. 1A-1C is characterized as having a substantially straight free edge 146a,b and an arcuate cusp edge 148a,b.

A contoured area is provided within the defined shape 140a,b. The contoured area comprises first and second elevations 142a,b and 144a,b and a transition defined therebetween. In the embodiment depicted in FIGS. 1A-1C, the first elevation 142a,b is provided as a substantially planar surface that is higher than or raised above the second elevation 144a,b, such that compression of a tissue disposed between the first and second plates 110, 120 would result in a tissue having at least two different thicknesses. Thus, the area of the tissue compressed between the first elevation 142a,b is thinner than the area of the tissue compressed between the second elevation 144a,b.

Figure 1D:
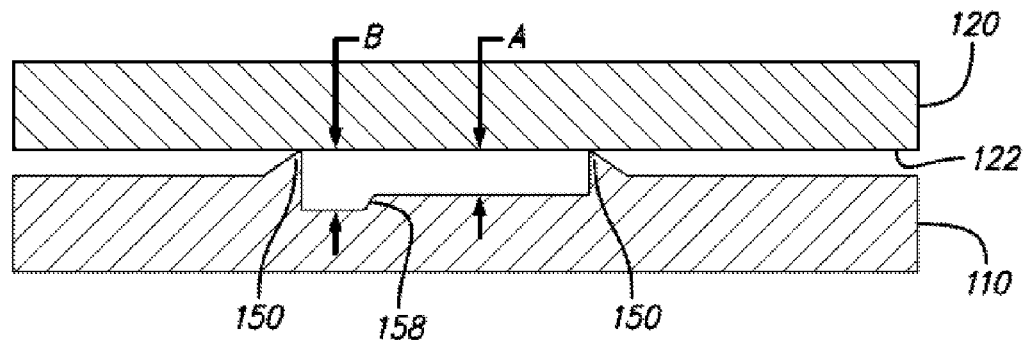
FIG. 1D is a cross-sectional view of an embodiment of a coupled first and second compression plates along axis 1D-1D of FIG. 1C.
Figure 1E:
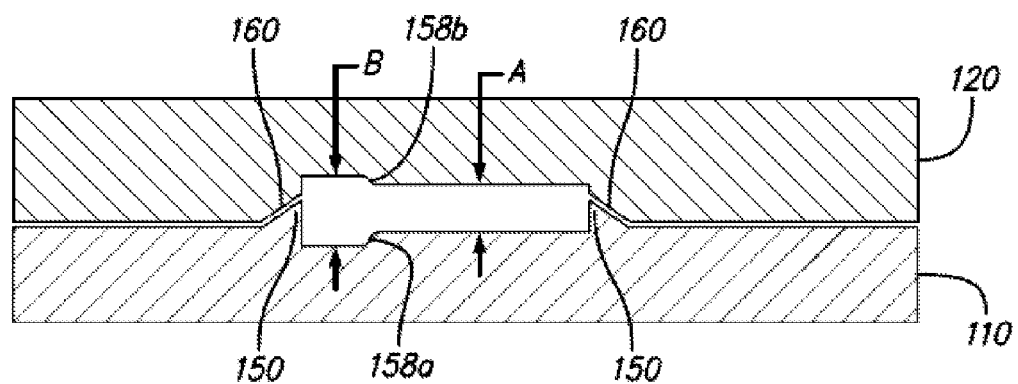
FIG. 1E is a cross-sectional view of an embodiment of a coupled first and second compression plates along axis 1E-1E of FIG. 1C.

A blade 150 can additionally be provided on one of the first and second plates 110, 120. The blade 150 is depicted in FIGS. 1A and 1C as being disposed on the first bottom plate 110, with a corresponding recess 160 being defined in the second top plate 120 to receive the blade 150 and to permit direct contact between the facing surfaces of the first and second plates 110, 120 during compression as shown in FIG. 1E. FIG. 1E depicts the cooperation between the blade 150 of the first plate 110 and the corresponding recess 160 of the second plate as the first and second plates 110, 120 are actuated towards one another. In an alternative embodiment as depicted in FIG. 1D, only the first plate 110 can comprise the defined shape and the contoured area and the second plate 120 can be provided as a substantially flat and planar surface 122.

Figure 9A:
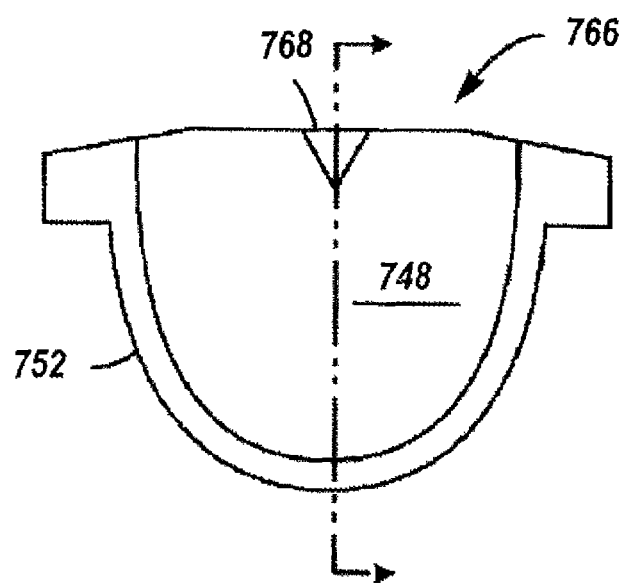
FIG. 9A is a plan view of a prosthetic heart valve leaflet having thickened peripheral edge in areas where sutures penetrate for attachment to a structural stent as well as a thickened triple point area in the free edge simulating nodules of Arantius.

Compression of a biological tissue between the first and second plates 110, 120 results in a tissue having two different thicknesses, as indicated by A and B, and a continuous transition 158 between A and B. A continuous transition, as used herein, can be broadly understood to mean a transition which is curved or devoid of any sharply angled surfaces which are 90 degrees or less or, alternatively, devoid of any angled surfaces. The embodiments depicted in FIGS. 1D and 1E will result in a compressed tissue having a continuous transition which is curved and devoid of any angled surfaces, whereas the compressed tissue depicted in FIGS. 7A, 8A and 9A show a continuous transition which is devoid of any sharply angled surfaces which are 90 degrees or less. The contoured tissue resulting from compression by the first and second plates 110, 120 of FIG. 1D will be substantially flat on one side and contoured on the other side, whereas the contoured tissue resulting from compression by the first and second plates 110, 120 of FIG. 1E will be substantially symmetrical along a bisecting plane across the compressed tissue. In both embodiments of FIGS. 1D and 1E, the tissue will be simultaneously compressed and cut to the defined shape by the contacting blade.

Static compression is not believed to be sufficient to restructure the collagen fiber density and orientation to produce a tissue that is uniform and that maintains the reduced thickness in the compressed state. Accordingly, an energy source 130 is depicted as being coupled to the first plate 110. It is understood that the energy source 130 can be connected to either one or both of the first and second plates 110, 120. The energy source 130 is configured to deliver one or a combination of thermal, ultrasound, electromagnetic, vibrational, hydraulic, piezoelectric, pneumatic, and acoustic and sound energy. The provision of energy to the biological tissue during compression is believed to facilitate a more effective collagen restructuring, as static compression without the provision of energy is believed to produce a tissue of non-uniform thickness over the compressed sample. This may be the case because the collagen fibers may not realign during static compression and thus do not become more isotropic after compression. As a more uniform tissue across a given compressed area is desired, the provision of energy during compression is believed to produce this result.

In accordance with a first aspect, the energy source 130 delivers vibrational energy to the tissue during compression. The application of directed vibrational energy during compression is believed to influence collagen fiber restructuring and also to make the collagen fiber alignment and density more uniform and predictable. While the tissue is being compressed under a high load, e.g., 1,000 lbs, vibrational energy can be sent through the tissue by one or both of the compression plates 110, 120. The vibration source can be a vibrating clamp (480, FIG. 4B) on the plates or a vibrating platform under the plates. While the tissue fibers are compressed, the vibration will cause shifting of the collagen fibers, possibly helping them fit together more tightly and thus permit compression to yet a more reduced thickness than would be possible in the absence of vibration. The shifting of the collagen fiber may also potentiate fiber redistribution so that the fiber density becomes more consistent in the tissue. Additionally, directing the vibration in certain directions can help the collagen fiber to realign to a more preferred orientation, making the tissue properties more predictable.

Figure 2A:
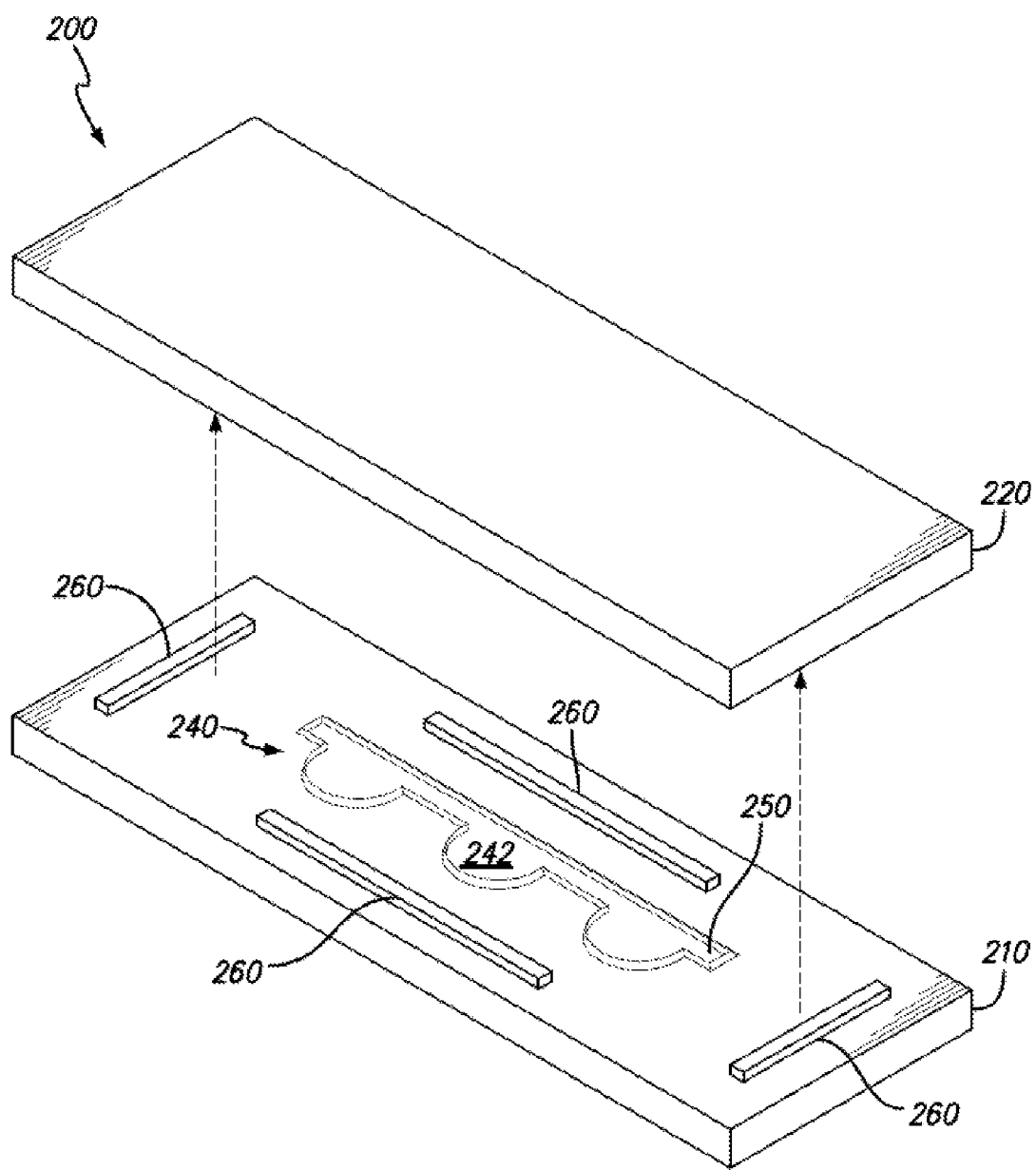
FIG. 2A is an exploded perspective view of an embodiment of a tissue compression assembly comprising spacers.
Figure 2B:
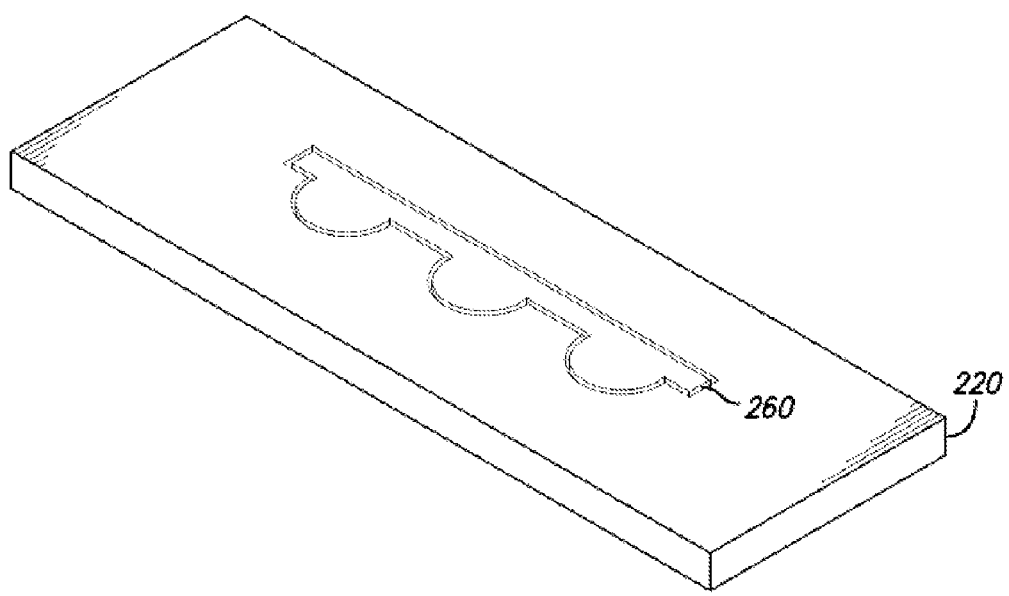
FIG. 2B is a perspective view of a bottom surface of the top plate of FIG. 2A.

FIGS. 2A and 2B depict another embodiment of a tissue compression assembly 200 comprising a first plate 210 and a second plate 220. The first plate 210 is depicted as comprising a defined shape in the form of three heart valve leaflets having a recessed area 242 and a blade 250 provided in the defined shape. The second plate 220 comprises a recess 260 corresponding to the blade 250 disposed the first plate 210 and configured to receive the blade 250 within the recess 260 as the first and second plates 210, 220 are actuated toward each other in compressing engagement. Spacers 260 are provided to control the thickness of the resulting compressed and contoured tissue. The advantage of having a tissue compression assembly 200 comprising a plurality of heart valve leaflets is that it will obviate the need to suture each individual heart valve leaflet together. The spacers 260 can be provided in a range of thicknesses depending on the depth of the recessed area 242. Thus, for more thinly compressed tissues, a correspondingly thinner spacer can be used and for more thickly compressed tissues, a correspondingly thicker spacer can be used. The defined shape of the three heart valve leaflets can have the same or similar contouring as depicted in FIGS. 1A-1E such that the tissue is compressed to two different thicknesses and has a continuous transition between the two thicknesses. Additionally, an energy source can also be provided to one or both of the first and second plates 210, 220 to ensure to substantially maintain the tissue in its compressed state after the compression.

Figure 3A:
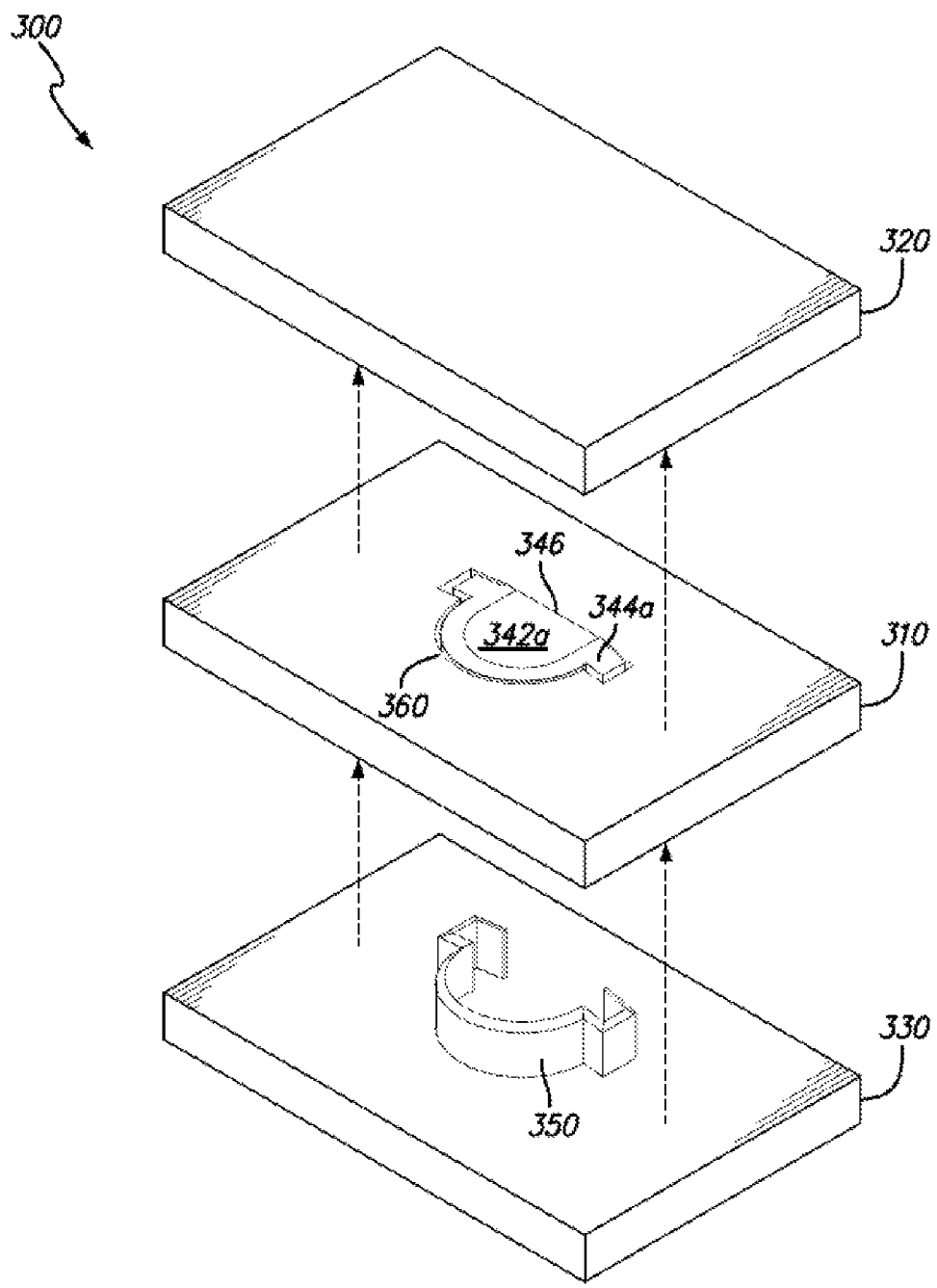
FIGS. 3A and 3B are exploded perspective views of an embodiment of a tissue compression assembly and cutting plate.
Figure 3B:
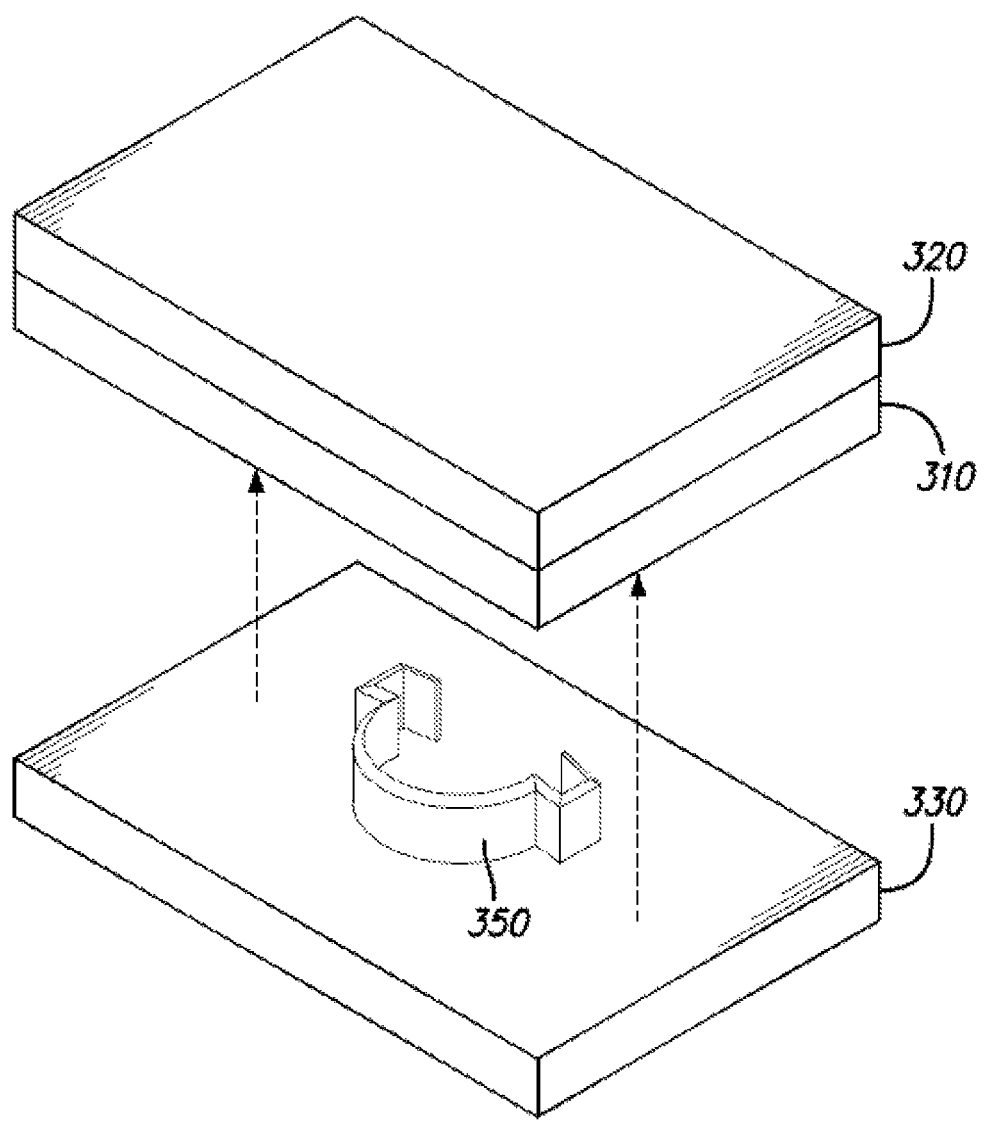

FIGS. 3A-3B depict yet another embodiment of a tissue compression assembly 300 in which blade 350 is provided separately on a third plate 330. Thus, the first and second plates 310, 320 are similar in substantial respects to the plates of FIGS. 1A-1C, except that the first plate 310 comprises a gap 360 surrounding a substantial portion of the defined shape to receive the blade 350 of the third plate 330. As depicted in FIG. 3B, the tissue can be contoured by compression between the first and second plates 310, 320 and the blade 350 of the third plate 330 can be inserted into the gap 360 of the first plate 310 to cut the contoured and compressed tissue to the desired shape. As can be seen in FIG. 3A, the gap 360 in the first plate 310 does not extend across the entirety of the defined shape so as to ensure that the defined shape remains supported by first plate 310. In a preferred embodiment, all three plates, 310, 320 and 330 are brought together and compressed, such that the tissue is compressed prior to or simultaneously with the cutting by the blade 350 disposed from the third plate 330. In another embodiment, the first and second plates 310, 320 apply the compression to the tissue disposed therebetween and the third plate 330 actuated towards the coupled first and second plates 310, 320 to cut the compressed tissue therebetween (see FIG. 3B). It is understood that an energy source can be provided in the manner as described and depicted herein.

Figure 4A:
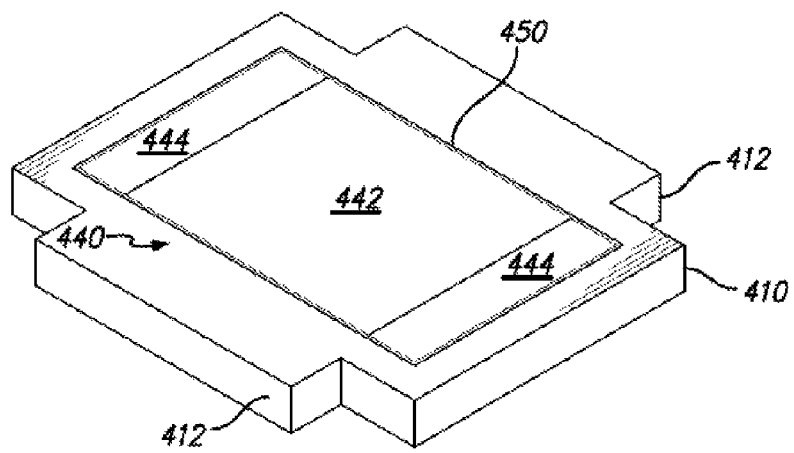
FIG. 4A is a perspective view of one of a pair of tissue compression plates having a defined rectilinear shape.
Figure 4B:
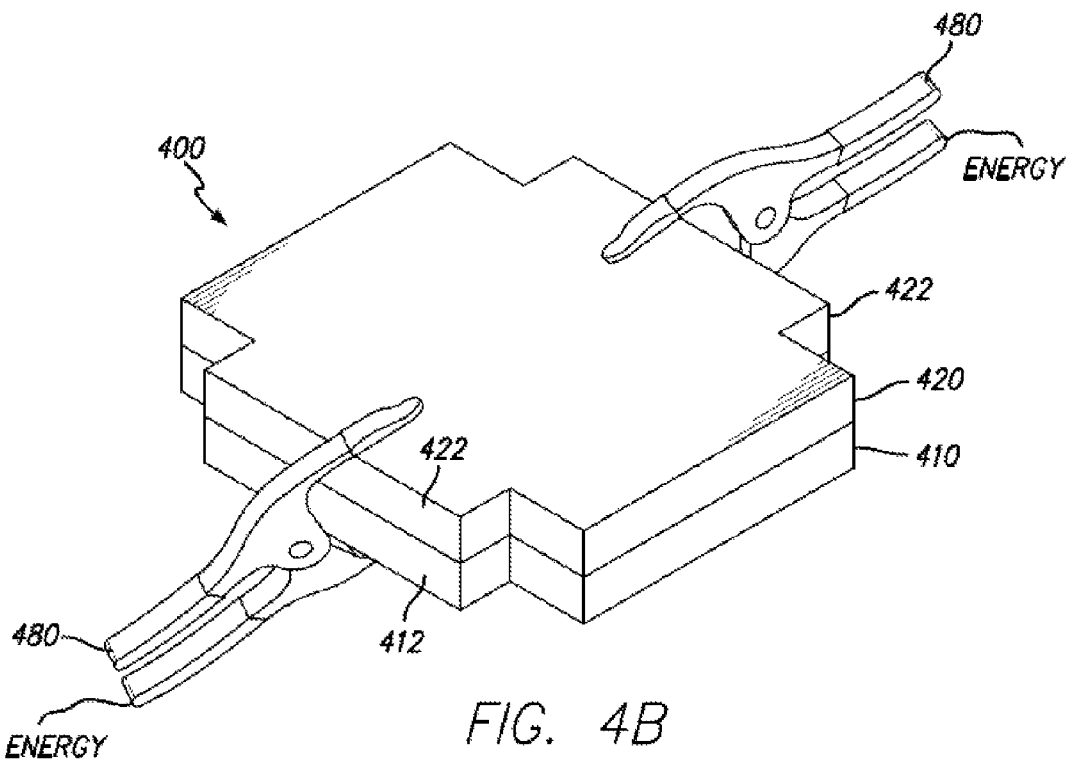
FIG. 4B is a perspective view of the pair of tissue compression plates coupled together with energized clamps.

FIGS. 4A-4B depict yet another embodiment of a tissue compression assembly 400 comprising first and second plates 410, 420, wherein the first plate 410 comprises a rectilinear defined shape 440 having areas of different elevations 442, 444. The first elevation 442 can be higher than the second elevation 444 or vice versa. A tissue contoured in accordance with the tissue compression assembly 400 would be appropriate for fabricating, for example, an aortic conduit. The first and second plates 410, 420 each have an area which is shaped to receive a vibrating clamp 480. The directed vibration energy is applied by a vibrating clamp 480 at one or both ends 422 of the compression plates 410, 420. The clamp 480 sends vibrations through the plates from one side to the other. In another embodiment (not depicted) a vibrating platform can be provided upon which the compression plates 410, 420 are placed. The entire platform can vibrate and the vibrations can be consistent over the platform or can be applied in waves, starting from one side of the platform and moving to the opposite side. Additionally, the vibration source can be the compression load head or actuator (not depicted) itself. The head that comes down to apply the compressive load on the plates 410, 420 can vibrate uniformly from one side to the other.

As with all the embodiments described herein, vibrational energy, thermal energy, ultrasound energy, electromagnetic energy, hydraulic energy, piezoelectric energy, pneumatic energy, and acoustic or sound energy can also be delivered to the tissue individually, sequentially, or in any number of combinations during compression and contouring.

Thermal energy is believed to weaken bonds in the tissue and to allow it to be compressed more easily. The tissue can be cooled during or after compression to set the new thickness. The heating source can be provided in multiple ways, such as by providing heated coils within or on top of one or both of the contoured plates, or lay using a heated liquid bath.

Ultrasound transducers can also be coupled to or otherwise associated with one or both of the first and second plates, or a liquid bath. Ultrasound energy is believed to create small cavities in the tissue to help break some of the bonds in the tissue. Prolonged exposure to ultrasound energy will also increase the temperature of the tissue, making it easier to break bonds. Applying a mechanical compression load while heating and/or applying ultrasound energy to the tissue can increase compressibility and reduce rebound. Ultrasound energy can be applied to the tissue before, during and/or after the compression. In a preferred embodiment, ultrasound energy is applied at least during the compression.

Electromagnetic energy can also be provided as an energy source during compression and contouring. The electromagnetic energy can be microwave or RF or infrared and provided by a source such as an RF or microwave antenna embedded in a non-conducting plate or a printed circuit antenna insulated from the tissue itself. The electromagnetic energy can be delivered alone or in combination with any one or more of the other energy sources. In a preferred embodiment, electromagnetic energy is applied before, during and/or after the compression. In a preferred embodiment, electromagnetic energy is applied at least during the compression.

Figure 5:
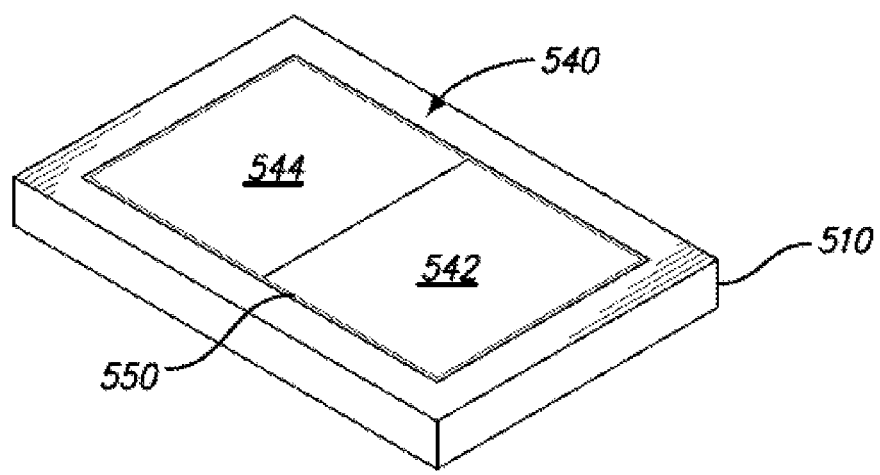
FIG. 5 is a perspective view of a further embodiment of a tissue compression plate having a rectilinear defined shape.
Figure 6:
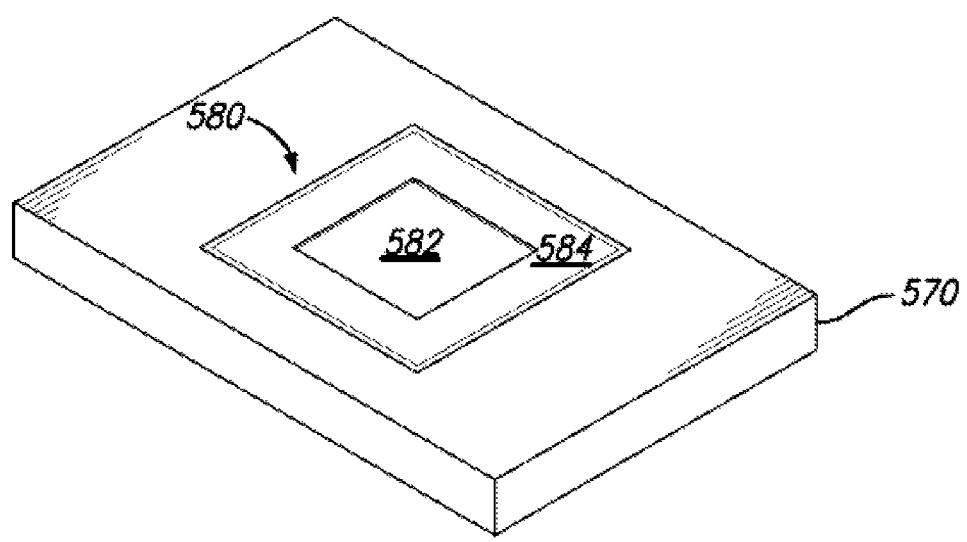
FIG. 6 is a perspective view of yet a further embodiment of a tissue compression plate having a rectilinear defined shape.

FIGS. 5-6 depict yet further alternate embodiments of a first plate having different defined shapes.

In FIG. 5, the first plate 510 of a tissue compression assembly is provided as having a defined shape 540 of a rectilinear polygon having two different elevations 542, 544 and a blade 550 surrounding the defined shape. A second plate (not depicted) can be provided having the mirror image of the defined shape 540 of the first plate 510, including the two different elevations 542, 544. Alternatively, the second plate can be a substantially flat plate, preferably comprising grooves to receive the blade 550 provided on the first plate 510.

In another embodiment, the defined shape can be a rectilinear polygon in which about the first elevation is defined in an area constituting about half of the rectilinear polygon and the second elevation is defined on a remaining portion of the rectilinear polygon.

In FIG. 6, the first plate 570 comprises the defined shape 580 of a square having different elevations 582, 584. Again, a second plate (not depicted) can be provided having the mirror image of the defined shape 580 including the different elevations 582, 584. Alternatively, the second plate can be a substantially flat plate, preferably comprising grooves to receive a blade provided on the first plate. The first elevation 582 can be raised above the second elevation 584 so as to produce a compressed tissue having a thinner central area corresponding to the first elevation 582 and a thicker periphery corresponding to the second elevation 584. Alternatively, the second elevation 584 can be raised above the first elevation 582 so as to produce a compressed tissue having a thinner peripheral area and a thicker central area.

FIGS. 7-9 illustrate alternative thickness profiles in pericardial tissue prosthetic heart valve leaflets from the selective thinning processes described herein. Each of the leaflets is shown in plan view and has an arcuate cusp edge 740, a generally straight free edge 742 opposite the cusp edge 740, and a pair of oppositely-directed tabs 744 at either end of the free edge. Each of the tabs 744 includes a tapered side 746 which transitions to the free edge 742. A central portion 748 in each of the leaflets forms the fluid occluding surface that oscillates in and out of the flow stream to alternately open and close the valve. This shape is exemplary only, and other leaflet shapes are known. Each of the leaflets shown in FIGS. 7-9 have the same shape, and thus the same element numbers for the shape characteristics will be used.

FIG. 7A illustrates a leaflet 750 having a thickened peripheral edge region 752 in areas where sutures penetrate for attachment to a structural stent (not shown). More particularly, the thickened peripheral edge region 752 extends around the entire cusp edge 740 and up into at least a portion of the tabs 744. As mentioned, these are areas in which sutures are used to attach the leaflet to a supporting stent or skirt. The thickness of the peripheral edge region 752 can be up to 700 microns, preferably about 250-700 microns. At the same time, the central portion 748 is formed to have a relatively small thickness, thus facilitating a smaller delivery profile for valves that are compressed. For instance, a uniform thickness of about 100 to 250 microns for the central portion 748 is believed particularly useful to reduce the crimped profile of collapsible/expandable valves, though uniform thicknesses between 250-500 microns can be suitable.

Figure 9B:
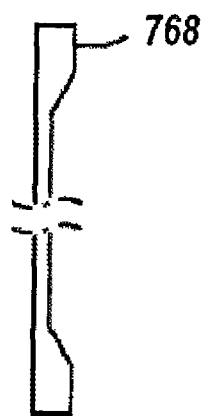
FIGS. 9B and 9C are sectional views through a radial midline of the leaflet of FIG. 9A showing two different thickness profiles.

FIGS. 7B and 7C are sectional views through a radial midline (vertical) of the leaflet of FIG. 7 showing two different thickness profiles. FIG. 7B illustrates a gradual ramp 754 between the thick edge region 752 and thinner central portion 748. The ramp 754 is shown linear, although other contours such as curved or gradually stepped can be used. In contrast, FIG. 7C illustrates the thicker peripheral edge region 752 transitioning to the thinner central portion 748 at a relatively abrupt step 756. It is believed the more gradual ramp 754 depicted in FIG. 7B provides a more desirable stress distribution and flow over the leaflet than the step 756. It is possible to provide gradual and continuous transitions by shaping the transition between the two elevations provided in the first and second plates in a curved manner, devoid of sharply angled areas. As depicted in FIGS. 7B, 8B and 9B, the transition between the first and second elevations is continuous insofar as it is angled ($\theta_1$) at greater than 90 degrees. In contrast, FIGS. 7C, 8C, and 9C depict the transition between the first and second elevations is regarded as non-continuous insofar as it is angled ($\theta_2$) at 90 degrees or less.

FIG. 8A is a plan view of a prosthetic heart valve leaflet 758 having a thickened peripheral edge region 752 as seen in FIG. 7A, as well as a thickened strip 760 along the free edge 742. Prosthetic heart valves sometimes fail from elongation of the free edge of the leaflet where the leaflets come together, or coapt, which ultimately may cause prolapse of the valve. Providing the thickened strip 760 along the entire free edge 742 reduces the risk of elongation, as the stresses experienced by free edge are proportional to its thickness. FIGS. 8B and 8C again show two different thickness profiles for the leaflets of FIG. 8A, wherein the thickened peripheral edge region 752 and thickened strip 760 can transition to the thinner central portion 748 at a continuous transition 762 (FIG. 8B) or steps 764 (FIG. 8C).

FIG. 9A illustrates a heart valve leaflet 766 again having the thickened peripheral edge 752 in areas used for attachment to a structural heart valve stent. In addition, the leaflet 766 has a thickened triple point area 768 in middle of the free edge 742 simulating a nodule of Arantius. To clarify, the so-called triple point in a heart valve leaflet is the point where the leaflet comes together (coapts) with the other leaflets in the center of the flow orifice. Because the three leaflets curve into the middle, a gap therebetween at the triple point can be sufficient to cause regurgitation. In native leaflets, the center of the free edge sometimes has a thickened area known as the nodules of Arantius that tends to fill the gap at the triple point. When using uniform thickness pericardial tissue for the leaflets, leakage can only be avoided by having a long coapting surface that requires extra leaflet material. However, that can adversely impact the ability to compress a valve to a low profile, and sometimes results in distortion of the leaflet when it closes which might result in early calcification. By producing a thickened triple point area 768 in each of the leaflets, a nodule of Arantius can be simulated. The exemplary triple point area 768 is shown as a small triangle in the center of the free edge 742, although the shape could be curved such as a semi-circle, or other shapes. Furthermore, the triple point area 768 can be combined with the thickened strip 760 along the free edge 742, such as seen in FIG. 8A. Indeed, any of the various thickened regions described herein can be combined with other regions for a desired effect.

Figure 9C:
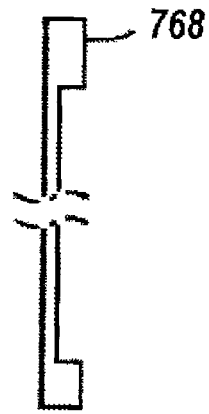

FIGS. 9B and 9C show two different thickness profiles for the leaflet 766. FIG. 9B shows gradual transitions between the thinner central portion 748 and both the thickened peripheral edge 752 and the thickened triple point area 768, while FIG. 9C shows abrupt steps at the same locations.

Figure 10:
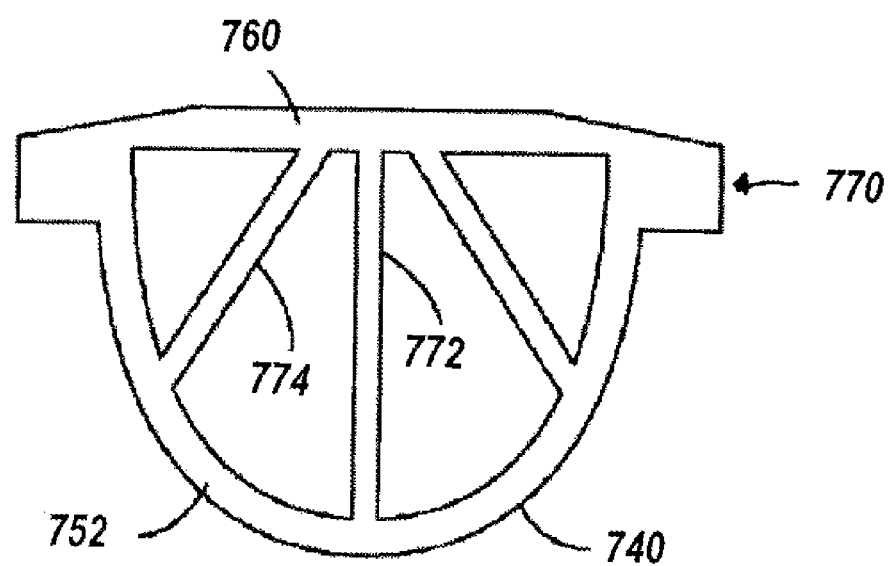
FIG. 10 illustrates in plan view an alternative leaflet having a thickened peripheral edge region, a thickened strip along the free edge, and a plurality of thickened radial strips extending from the free edge to the cusp edge.

FIG. 10 illustrates an alternative leaflet 770 of the present application that can help reduce sagging in leaflets, which has been found as a cause of failure in some prosthetic heart valves. Resistance to leaflet elongation is directly proportional to leaflet thickness along radial stress lines. Therefore, in addition to a thickened peripheral edge region 752 and a thickened strip 760 along the free edge 742, the leaflet 770 includes a plurality of thickened radial strips 772, 774 extending from approximately the middle of the free edge 742 to the arcuate cusp edge 740. The "radial lines" in this sense are drawn as if the cusp edge 740 was the edge of a circle centered in the middle of the free edge 742, though it should be understood that the cusp edge 740 is not defined by a single arc, and may not be centered at the free edge 742. Typically, prosthetic leaflets are symmetric about a radial midline, however, and thus one preferred arrangement includes a thickened radial strip 772 along the midline (vertical), and symmetric thickened radial strips 774 on either side of the vertical strip 772. In the illustrated embodiment, there are three strips; a midline strip 772 and two radial strips 774 at approximately 30° angles from the middle strip. It should also be noted that as illustrated, the various thickened strips around the leaflet are of approximately the same width, though such does not have to be the case. For example, the cusp edge strip 760 and radial strips 772, 774 can be substantially thinner than the edge region 752 through which sutures must pass.

One contemplated sequence for conditioning tissue includes first cross-linking the tissue (e.g., bovine pericardium) with a glutaraldehyde-buffered solution. Next, the tissue can be heat treated using a process such as disclosed in U.S. Pat. No. 5,931,969 to Carpentier, issued Aug. 3, 1999, the disclosure of which is expressly incorporated herein by reference in its entirety. Subsequently, the thickness of the tissue can be reduced using any of the methods disclosed in the present application. Finally, the thinner tissue can be treated with a capping and/or reducing agent to mitigate later in vivo calcification; this can also include treating with a glycerol/ethanol solution such as is disclosed in U.S. Pat. No. 7,972,376, issued Jul. 5, 2011 to Edwards Lifesciences Corp., the content of which is incorporated herein by reference in its entirety. The thinner tissue can also be at least partially dehydrated or dried by other chemical or non-chemical means to permit storage of the compressed and contoured tissue in a non-fluid environment. Alternatively, the tissue can be at least partially dehydrated or dried prior to compression. Methods of treating tissue to at least partially dehydrate or dry the tissue, as compared to its native state, are disclosed in U.S. Pat. No. 8,007,992, issued Aug. 30, 2011 to Edwards Lifesciences, Corp. and U.S. Pat. No. 6,534,004, issued Mar. 18, 2003 to The Cleveland Clinic Foundation, the entire contents of which are incorporated herein by reference in their entireties.

For prosthetic heart valve leaflets, the compressed and contoured leaflets are attached to a surrounding heart valve support frame or other such components, and sterilized such as with ethylene oxide. After the tissue has been compressed and contoured to reduce its thickness, calcification nucleation sites (e.g., aldehydes and Schiff bases) can be exposed which creates a propensity for calcification. Treating with a capping agent (e.g., ethanolamine) a reducing agent (e.g., sodium borohydride) and a collagen preserving agent (e.g. glycerol) caps the nucleation sites and preserves the collagen integrity. This allows the tissue to be as durable as it was before it was reduced in thickness. Furthermore, this process will also allow the tissue to be stored in a non-liquid environment. In other words, the process is especially suitable for dry storage of the tissue.

As noted above, the tissue can be at least partially cross-linked or "fixed." Cross-linking the collagenous matrix provides stability prior to implantation to retard degeneration. Further, the fixation process generally operates by blocking reactive molecules on the surface of and within the donor tissue, thereby rendering it substantially non-antigenic and suitable for implantation. Fixing bioprosthetic tissue typically involves contacting the tissue with a cross-linking agent, normally a solution. Exemplary fixing solutions for bioprosthetic tissue such as bovine pericardium include glutaraldehyde, formaldehyde, other aldehydes, EDC, polyethylene glycol, etc. Other ways to fix tissue exist, including heating, irradiating, etc. The fixing step can help maintain the pericardium in a particular three-dimensional form if undertaken after the membrane is otherwise prepared.

It should be understood that although cross-linking the tissue results in a somewhat easier to handle work piece, the compressing and contouring can occur prior to cross-linking as well. Likewise, bulk tissue sheet can be compressed and contoured first before or after fixing, or leaflets can first be cut from the bulk membrane which are then compressed and contoured before or after fixing.

Accordingly, the biological tissue can first be fixed with glutaraldehyde or other fixing agent before the compression and contouring. In one embodiment, the tissue can be soaked with a fixative before the compressing. The fixative can be glutaraldehyde and/or a 0.1% polyetheramine solution having an average molecular weight of about 600 and a pH of about 6 to 9. The tissue can be rinsed with a saline before the soaking and after the compression.

This first fixation step stabilizes the biomechanics of the tissue and preserves the natural "crimp" structure of the collagen.

In a preferred embodiment, a second fixation step is provided after the first fixation step and before, during and/or after the compressing and contouring. Infusion with a second fixing agent of sufficient chain length to allow spanning of large inter-fibril domains can result in a stable tissue membrane. Second fixative agents include di- or poly-amine material of substantial chain length can be employed. Other cross-linking material to span large inter-fibril domains include both linear and branched polyethyleneimine, polyvinyl alcohol and various Jeffamine polymers, polyetheramines, di- and poly-amines, polyurethanes, polyepoxies, polysiloxanes, polyacrylates, polyesters, poly block isobutylene-co-maleic acid, collagen, elastin, fibrin, hyaluronic acid, dextrin, genapin, di or poly-alkynes, di- or poly-azides, and tannins. Alternatively, the tissue can be oxidized with, for example, sodium chlorite to convert the newly formed aldehydes to carboxylic acids. These can then be coupled with the above amines using EDC chemistry. Compression can occur either at the beginning of the process, after infusion with a second fixing material, or both. The tissue can be capped and reduced following the first fixation step, or alternatively, the compressed and cross-linked tissue can be stabilized by capping and borohydride reduction after the contouring.

In a preferred embodiment, the tissue is treated with a first fixative before the compressing and then treated with a second fixative before, during or after the compressing, preferably during and, more preferably both during and after the compressing. To that end, one or both of the first and second plates used to compress the tissues, as disclosed herein, can be made of a porous substrate to permit the infusion of or submission in a solution comprising one or both of the first and second fixative during the compression.

In a preferred embodiment, the second fixing cross-links the biological tissue by utilizing a combination of an anchor compound and a difunctional linking compound, each one of which comprises complementary ones of a bio-orthogonal binding pair. One advantage is that the reaction between the bio-orthogonal binding pair is highly specific only to each other, thereby reducing or even eliminating the possibility of undesired side reactions between any one of the bio-orthogonal binding pair with tissue functional groups present in or native to biological tissue.

As used herein, "bio-orthogonal binding pair" refers to a pair of functional groups which react with and couple one another within a biological tissue. The reaction and coupling between complementary ones of the bio-orthogonal binding pair is mutually exclusive such that each one of the bio-orthogonal binding pair does not react with any tissue functional groups or with any functional groups found inside living systems.

As used herein, "tissue functional groups" refer to functional groups which are native to biological tissue and, more particularly, in collagenous tissue, such as, for example, cardiac valves, blood vessels, skin, dura mater, pericardium, small intestinal submucosa ("SIS tissue"), ligaments and tendons. Exemplary tissue functional groups include amines, hydroxyls, sulfhydryls, aldehydes, and carboxylic acids.

In a preferred embodiment, the bio-orthogonal binding pair comprises an azide and an acetylene. It is understood that the azide and acetylene groups of the bio-orthogonal binding pair can be present as either a terminal or an internal group within an anchor compound or a linking compound used in accordance with the method. While the reaction of the bio-orthogonal binding pair itself is specific to one another, one or both of the anchor compound or the linking compound can comprise additional functional groups, such as those which react with tissue functional groups which can be reactive with other functional groups, such as tissue functional groups. However, it is understood that the additional functional groups of the first or linking compound are not reactive with either one of the bio-orthogonal binding pair.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. An assembly for providing a contoured biological tissue, the assembly comprising:
   a first plate configured to receive a biological tissue;
   a second plate having a surface and being configured to apply a compressive force on the biological tissue disposed on the first plate;
   wherein one or both of the first and second plates comprise a defined shape and a contoured area within the defined shape, the contoured area comprising at least first and second elevations and a continuous transition between the first and second elevations; and
   one or more energy sources associated with one or both of the first and second plates, the one or more energy sources delivering energy when the the biological tissue is compressed between the first and second plates;
   wherein the defined shape includes a peripheral edge region and a central region within the peripheral edge region, and
   wherein a first distance between the first and second plates along at least a portion of the peripheral edge region is greater than a second distance between the first and second plates along at least a portion of the central region.

2. The assembly of claim 1, wherein the one or both of the first and second plates are porous.

3. The assembly of claim 1, wherein the defined shape is one or a plurality of heart valve leaflets and wherein the heart valve leaflets each has a substantially straight free edge and an arcuate cusp edge.

4. The assembly of claim 3, wherein the first elevation is defined along the arcuate cusp edge and the second elevation is located between the arcuate cusp edge.

5. The assembly of claim 4, wherein the first elevation is higher relative to the second elevation.

6. The assembly of claim 4, wherein the second elevation is higher relative to the first elevation.

7. The assembly of claim 1, further comprising a spacer disposed between the first and second plates, the spacer controlling a thickness of the compressed biological tissue.

8. The assembly of claim 1, further comprising a blade corresponding substantially to the defined shape on the first plate.

9. The assembly of claim 1, wherein the energy delivered by the one or more energy sources is one or a combination selected from the group consisting of: thermal, ultrasound, electromagnetic, vibrational, hydraulic, piezoelectric, pneumatic, and acoustic or sound.

10. The assembly of claim 9, wherein the energy is thermal energy and wherein the one or more energy sources is one or a combination selected from the group consisting of: thermal coils disposed within the first plate, thermal coils disposed within the second plate, and a liquid bath.

11. The assembly of claim 9, wherein the energy is ultrasound energy and wherein the one or more energy sources is an ultrasound transducer associated with one or both of the first and second plates or with a liquid bath.

12. The assembly of claim 9, wherein the energy is electromagnetic energy and wherein the energy source is a RF or microwave antenna embedded in a non-conducting plate or a printed circuit antenna insulated from the tissue.

13. The assembly of claim 9, wherein the energy is vibrational energy and wherein the one or more energy sources is a clamp coupled to one or both of the first and second plates, a platform in contact with one or both of the first and second plates, an actuator coupled to one or both of the first and second plates.

14. The assembly of claim 1, wherein the first plate comprises the defined shape and contoured area and the second plate comprises a substantially flat surface.

15. The assembly of claim 1, wherein the first and second plates each comprise the defined shape and the contoured area within the defined shape.

16. The assembly of claim 1, wherein the first distance is from about 250 to about 700 microns and the second distance is from about 100 to about 250 microns.

17. A method for preparing a contoured biological tissue comprising:
    compressing a layer of biological tissue between first and second plates to reduce a thickness of at least a portion of the tissue; and
    delivering energy from an energy source to one or both of the first and second plates during the compressing;
    wherein the tissue following the compressing has at least two areas of different thicknesses and a continuous transition within a defined shape.

18. The method of claim 17, further comprising treating the tissue with a first fixative to at least partially fix the tissue.

19. The method of claim 18, further comprising treating the tissue with a second fixative before, during or before and during the compressing.

20. The method of claim 19, wherein the second fixative is one or a combination selected from the group consisting of: polyvinyl alcohols, polyetheramines, polyethyleneimine, di- or poly-amines, polyurethanes, polyepoxies, polysiloxanes, polyacrylates, polyesters, poly block isobutylene-co-maleic acid, collagen, elastin, fibrin, hyaluronic acid, dextrin, genapin, di- or poly-alkynes, di- or poly-azides, and tannins.

21. The method of claim 17, further comprising soaking the tissue with a fixative, wherein the fixative is a 0.1% polyetheramine solution having an average molecular weight of about 600 and a pH of about 6 to 9.

22. The method of claim 17, wherein a first thickness is from about 250 to about 700 microns and a second thickness is from about 100 to about 250 microns.

23. The method of claim 17, wherein the step of treating the tissue with a first fixative to at least partially fix the tissue occurs before the compressing step.

24. The method of claim 17, wherein the step of treating the tissue with a first fixative to at least partially fix the tissue occurs during the compressing step.

25. The method of claim 17, wherein the step of treating the tissue with a first fixative to at least partially fix the tissue occurs after the compressing step.

* * * * *